United States Patent
Discko, Jr.

[11] Patent Number: 6,099,307
[45] Date of Patent: Aug. 8, 2000

[54] DENTAL CAPSULE FOR CONTAINING AND DISPENSING LOW VISCOSITY DENTAL MATERIAL AND METHOD OF FILLING AND APPLYING SAID LOW VISCOSITY MATERIAL

[75] Inventor: John J. Discko, Jr., Trumbull, Conn.

[73] Assignee: Centrix, Inc., Shelton, Conn.

[21] Appl. No.: 09/188,966

[22] Filed: Nov. 9, 1998

[51] Int. Cl.⁷ ................................................ A61C 5/04
[52] U.S. Cl. ............................................................. 433/90
[58] Field of Search ........................ 433/89, 90; 222/386, 222/326

[56] References Cited

U.S. PATENT DOCUMENTS

| | | |
|---|---|---|
| 3,581,399 | 6/1971 | Dragan . |
| 3,900,954 | 8/1975 | Dragan . |
| 4,198,756 | 4/1980 | Dragan . |
| 4,330,280 | 5/1982 | Dougherty et al. . |
| 4,384,853 | 5/1983 | Welsh . |
| 4,391,590 | 7/1983 | Dougherty . |
| 4,619,613 | 10/1986 | Dragan . |
| 4,767,326 | 8/1988 | Bennett et al. . |
| 4,963,093 | 10/1990 | Dragan . |
| 4,969,816 | 11/1990 | Drumm . |
| 5,100,320 | 3/1992 | Martin et al. . |
| 5,322,440 | 6/1994 | Steele . |
| 5,460,523 | 10/1995 | Schulman . |

*Primary Examiner*—Nicholas D. Lucchesi
*Attorney, Agent, or Firm*—Fattibene & Fattibene; Arthur T. Fattibene; Paul A. Fattibene

[57] ABSTRACT

A dental capsule or syringe and method for packaging, storing and/or dispensing a low viscosity or liquid-like dental material in which the liquid dental material is saturated in a sponge or cellular foam-like filler confined within the body portion or chamber of the dental capsule and sealed therein by a displaceable piston; and whereby the liquid dental material is dispensed therefrom by imparting a compressive force onto the sponge or foam filler, causing the liquid dental material to be squeezed and dispensed therefrom in a controlled manner by the displacement of the piston sealing the open end of the capsule. The discharge orifice may be sealed either by a suitable detachable sealing cap or by an integrally molded seal which must be severed prior to use.

13 Claims, 2 Drawing Sheets

DENTAL CAPSULE FOR CONTAINING AND DISPENSING LOW VISCOSITY DENTAL MATERIAL AND METHOD OF FILLING AND APPLYING SAID LOW VISCOSITY MATERIAL

FIELD OF THE INVENTION

The present invention relates generally to a dental capsule or cartridge and more specifically to a dental capsule or cartridge for containing and dispensing low viscosity dental materials.

BACKGROUND OF THE INVENTION

In the field of dentistry, the dispensing of various dental materials directly to a tooth surface to effect a tooth restoration has been known for some time. Reference is made to the placement of relatively high viscosity materials, e.g. filled composite resin material, directly to the site of the restoration using a syringe technique as disclosed in U.S. Pat. Nos. 3,518,399; 3,900,954 and 4,198,756. These patents disclose the syringing technique of utilizing a capsule filled with a high viscosity composite material from which the material was extruded by the displacement of a piston by means of a syringe or syringe gun.

Subsequently, others have adopted the technique of syringing the heavy or high viscosity dental materials as disclosed in U.S. Pat. Nos. 4,330,280 and 4,384,853. As the syringing technique and the use of unit dose capsules for dispensing heavy viscosity dental materials has gained recognition as the preferred method of placing heavy composite dental materials, various other capsule configurations have been made, as evidenced by U.S. Pat. Nos. 4,391,590; 4,619,613; 4,767,326; 4,963,093; 4,969,816; 5,100,320; 5,322,440 and 5,460,523, to cite a few. While the syringing technique and the use of preloaded capsules of the various known constructions proved satisfactory for the placement of heavy viscosity composite materials, difficulty has been encountered when using the syringe and capsule technique with the more fluent or very low viscosity dental materials that have a liquid state, as distinguished from the heavy viscosity dental materials that have a heavy paste-like consistency. This is because dental material having a very fluent liquid state could not be readily contained within the capsule as the material would tend to leak out of the capsule by gravity. Further, if the liquid or very fluent dental materials could be retained within the capsule, the dentist could not control the discharge of such liquid material from the capsule by syringing. As a result, the known capsule constructions were not generally suitable for dispensing very fluent or low viscosity dental material, e.g. those dental materials having a liquid-like consistency. For these reasons, dentists had to apply such fluid material by means of a brush or other suitable manual applicator, which required the dentist to repeatedly dip the brush or applicator into the fluid dental material, and then apply the material to a tooth, a tedious and time consuming procedure.

SUMMARY OF THE INVENTION

An object of this invention is to provide a capsule for containing a low viscosity liquid-like dental material from which the material can be syringed or dispensed in a controlled manner directly onto a tooth as needed.

Another object is to provide a capsule having a porous filler saturated with a low viscosity or liquid-like dental material for storing, shipping and dispensing the low viscosity dental material of liquid-like consistency whereby the liquid dental material saturated in the porous filler is dispensed by the application of a compressive force onto the porous filler so as to squeeze the dental material out of the capsule.

Another object of the invention is to provide a method of filling capsules with dental material having a low viscosity, liquid consistency and from which the low viscosity material can be dispensed directly onto a tooth in a controlled manner by syringing.

The foregoing objects and other features and advantages are attained by a dental capsule having a body portion defining a chamber that is open at one end and provided with a discharge nozzle connected to the other end thereof that terminates in a discharge orifice. Disposed within the body portion of the capsule is a filler formed of a sponge or open cell compressible foam formed of rubber or other inert synthetic or natural sponge-like material which is inserted into the body portion of the capsule. In accordance with this invention, the filler formed of a sponge or foam-like material is saturated with a low viscosity or liquid-like dental material, wherein the liquid-like dental material is retained within the filler. A displaceable piston is provided for sealing the open end of the capsule and confining the saturated filler within the capsule. If desired, the discharge orifice may be sealed by a displaceable sealing cap to protect the contents of the capsule from external contamination, e.g. dirt, dust and/or the like. It is understood that if the dental material saturated in the porous filler is light sensitive, the capsule, piston and sealing cap may be formed of light opaque material.

In accordance with this invention, the porous filler saturated with the low viscosity material is sized and shaped so that it can be readily fitted into the body of the capsule and then sealed therein by inserting the piston. To dispense the fluent material saturated in the porous filler in a controlled manner, the capsule is placed in a suitable syringe, e.g. a syringe of the type disclosed in U.S. Pat. Nos. 3,518,399 or 4,198,756; or a version thereof as disclosed in U.S. Pat. Nos. 4,330,280 or 4,384,853 patents, to effect the displacement of the piston. As the piston is displaced, a compressive force is imparted onto the saturated filler, causing the low viscosity material contained therein to be squeezed out and discharged through the discharge orifice in a controlled manner; depending upon the amount of compressive force that is imparted upon the porous filler by the piston.

IN THE DRAWINGS

DETAILED DESCRIPTION

Figure 1:
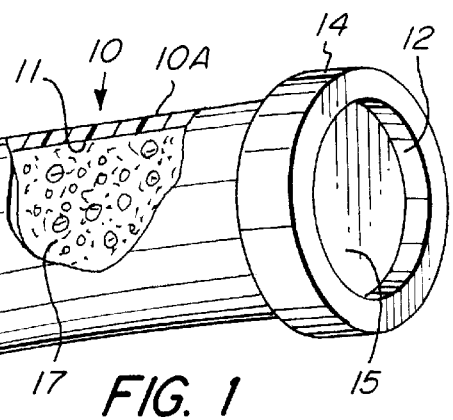
FIG. 1 is a side elevation view of a dental capsule embodying the invention and having portions thereof broken away.

Referring to the drawings, there is shown in FIG. 1, a capsule 10 which embodies the present invention. As shown, the capsule 10 has a body portion 10A defining a chamber or reservoir 11 that is open at one end as indicated at 12. In the illustrated embodiment of FIG. 1, a discharge nozzle 10B is connected to the other end of the reservoir or chamber 11 that tapers inwardly toward the discharge orifice 13. A laterally outwardly extending flange 14 circumscribes the open end of the capsule body portion 10A. In the assembled form of the capsule as seen in FIG. 1, a displaceable piston 15 is fitted into the open end 12 to seal the open end 12. While the described capsule 10 is illustrated as having a specific geometric shape, it will be understood that the specific shape or size of the capsule is not critical to the invention, as the capsule may assume any of the shapes or size that are disclosed in the patents hereinbefore cited and/or known to those skilled in the art. The invention to be described would be operative in any dental capsule that includes a body portion defining a chamber that is opened at one end and has a discharge nozzle connected to the other end and which open end is adapted to be sealed by a displaceable piston.

In accordance with this invention, a filler 17, formed of an inert porous material, e.g. a sponge, open cellular foam, cotton or other type of porous packing, is arranged to be sized and shaped to be fitted into the body portion 10A or reservoir 11. The filler 17 is saturated with a dental fluent, low viscosity or liquid-like material. It will be understood that the filler 17 may be saturated with the fluent dental material either before or after the filler is placed within the capsule body 10A. The open end 12 of the capsule 10 is then sealed by inserting therein a displaceable piston 15. If desired, the discharge orifice 13 may be sealed by a sealing cap 16 to protect the contents of the capsule from any contaminents such as dirt, dust and to prevent evaporation or drying of the dental material.

To dispense the fluid dental material that is saturated in the filler 17, the capsule 10 is placed in a suitable syringe. With the sealing cap 16 removed and upon the actuation of the syringe (not shown), the piston 15 is displaced so as to impart a compressive force onto the sponge-like filler 17, causing the fluid dental material contained therein to be squeezed out and dispensed through the discharge orifice 13. The amount of compressive force imparted by the piston 15 by the syringe and onto the filler 17 determines the amount of dental material that is dispensed. Thus, it will be apparent that the dentist or user can readily control the dispensing of the fluent material by regulating the amount of force that is applied by the piston 15 onto the filler.

Figure 2:
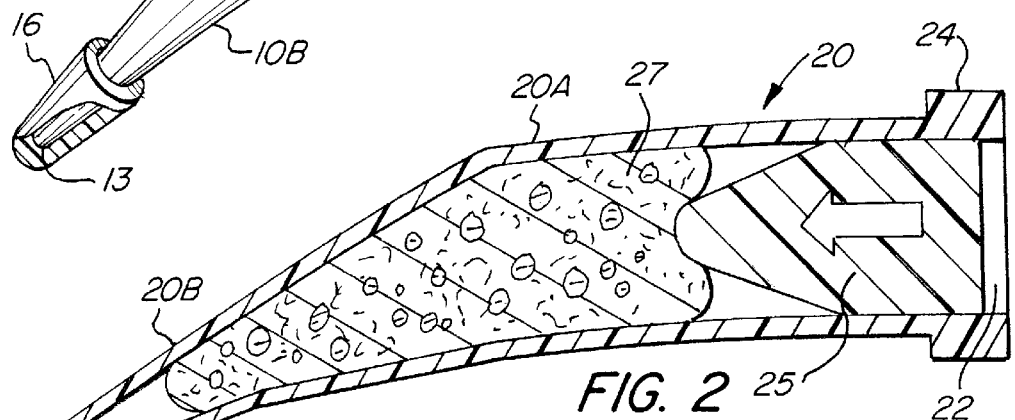
FIG. 2 is a sectional side view of a slightly modified embodiment of the invention.

FIG. 2 illustrates a slightly modified form of the invention. In this embodiment, the capsule 20 is virtually identical to that described with respect to FIG. 1 except the end of the discharge nozzle 20B is initially sealed as indicated at 21 in the molding of the capsule 20. In all other respects, capsule 20 is identical to that described with respect to the embodiment of FIG. 1. That is, the capsule 20 includes a body portion 20A having an open end 22 circumscribed by a flange 24 and a piston 25 for sealing the open end 22. Disposed within the body or reservoir 21 is a filler 27 saturated with a low viscosity dental material similar to that hereinbefore described.

To dispense the liquid or fluent material, the dentist or user must first cut off the sealed end 21 of capsule 20 to form the discharge orifice. In all other respects, the operation of capsule 20 is similar to that hereinbefore described.

Figure 3:
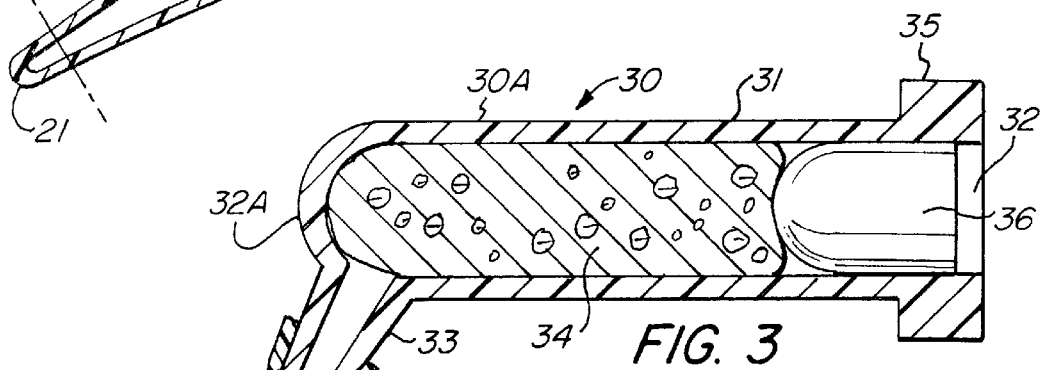
FIG. 3 is a side sectional view of another modified form of the invention showing the saturated filler in its normal expanded state.
Figure 4:
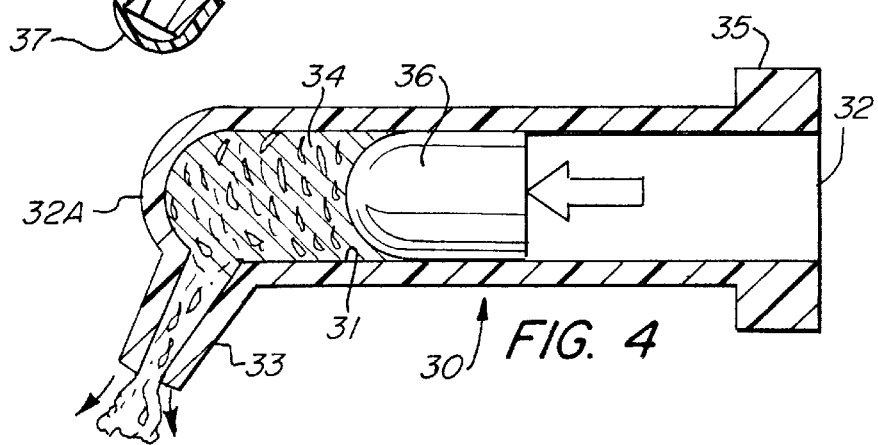
FIG. 4 is a side sectional view of FIG. 3 illustrating the saturated sponge or foam filler in a compressed state.

FIG. 3 illustrates another capsule formed of the parallel wall type, i.e. a capsule 30 having a cylindrical or parallel body portion 30A defining a reservoir 31. The capsule 30 is provided with an opening 32 at one end and a hemispherical closed end 32A, as illustrated, at the other end or conically shaped closed end (not shown). A discharge nozzle 33, angularly disposed relative to the longitudinal axis of the body portion 30A, is positioned adjacent the closed end 32A. Disposed within the reservoir 31 is a filler 34, saturated with the low viscosity or liquid-like dental material, similar to that described with respect to FIGS. 1 and 2, wherein the fluent dental material is retained or confined within the filler 34, e.g. the pores or cells of the porous filler 34. Like capsules 10 and 20, capsule 30 is provided with a lateral flange 35 circumscribing the open end 32 and having a piston 36 sealing the open end 32. A sealing cap 37 may be provided to seal the end of the discharge nozzle as hereinbefore described. In all other respects, the operation and the dispensing of the liquid or fluent dental material saturated within the filler or sponge 34 is similar to that hereinbefore described.

The capsules described herein are preferably molded of a suitable plastic material in the form or shape desired by molding. The cellular foam or sponge filler is then saturated with a low viscosity or liquid type dental material which is then placed within the body or reservoir portion of the capsule and sealed therein by the displaceable piston, whereby the fluid dental material is retained within the filler. For capsules having an open discharge orifice as shown in FIGS. 1 and 3, a sealing cap 16 or 37 respectively, may be employed to seal the orifice opening. In an alternate method, the filler may be first placed within the body of the capsule, and the liquid or fluent material is added thereafter, and before the piston is put in place to seal the end opening.

From the foregoing, it will be apparent that a liquid type dental material can be readily packaged, stored and dispensed from the capsule by syringing, whereby the low viscosity dental material can be readily dispensed in a controlled manner directly to the site of use in a simple and expedient manner. It will be noted that the structure described is relatively simple and positive in operation, whereby a liquid-like dental material can be directly dispensed in a controlled manner using a syringing technique. The sealing of the discharge opening, whether by a discrete sealing cap as in FIG. 1, or by an integrally molded end seal as in FIG. 2, prohibits any loss or evaporation of the liquid material contained within the cells or pores of the sponge or cellular foam filler.

Figure 5:
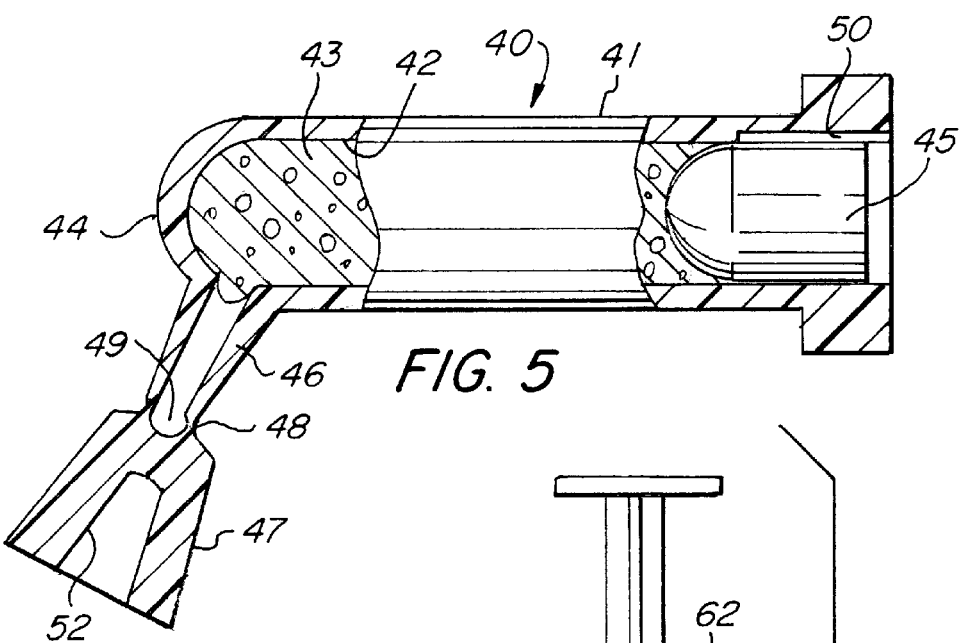
FIG. 5 is a side view of another embodiment of the invention.

The invention described herein can also be utilized in a capsule or cartridge having a discharge nozzle in which the orifice of the nozzle is sealed by a frangible sealing cap. An exemplary showing of such a capsule 40 is illustrated in FIG. 5. In this embodiment, the capsule 40 is provided with a cylindrical body portion 41 defining a reservoir chamber 42 for containing a saturated filler 43, as hereinbefore described. One end of the capsule body portion is closed by an end wall 44. It will be understood that the closed end wall 44 may be of any desired shape, e.g. hemispherical, conical or frusto conical or the like. The other end of the capsule body is opened to receive a sealing piston 45 as herein described. A discharge nozzle 46 is angularly offset in the illustrated embodiment. However, it will be understood that the discharge nozzle may be formed co-axially along the centerline of the capsule body portion 44.

In the embodiment of FIG. 5, the discharge end of the nozzle 46 is provided with an integrally formed sealing cap 47 which is joined to the end of the discharge nozzle 46 by a frangible or weakened portion 48, whereby the sealing cap 47 may be separated by "breaking" the sealing cap from the nozzle along the frangible or weakened portion 48. If desired, the sealing cap 47 may be provided with a means, e.g. a cavity or spike to reseal the discharge orifice 49 formed at the end of the discharge nozzle. Adjacent the open end of the capsule 40, there is provided one or more venting grooves 50, through which displaced air may be evacuated when the filler 43 is inserted into the closed body of the capsule 40. The displaceable piston 45 seals the open end of the capsule 40 and the venting grooves 50 when seated within the capsule as shown in FIG. 5.

In the illustrated embodiment, the sealing cap 47 is provided with a recess or cavity 52 which is sized and shaped to frictionally receive the discharge end of the nozzle to effect a resealing of the discharge orifice 49, if desired.

In operation, the liquid dental material retained in filler 43 is squeezed out when the piston 45 is displaced to impart a compressive force on the saturated filler 43 as hereinbefore described.

Figure 6:
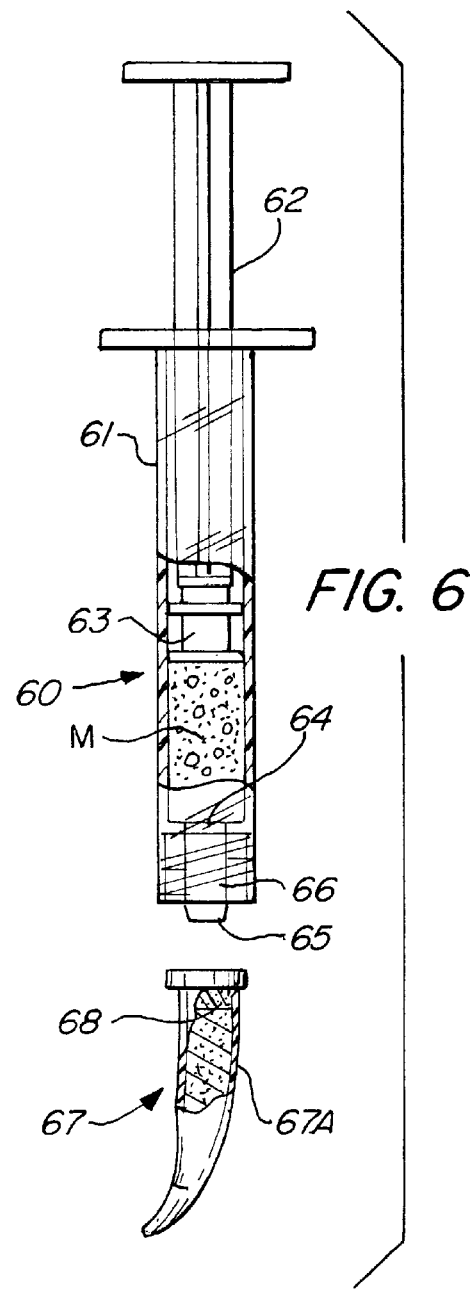
FIG. 6 is a side view of still another embodiment of the invention.

FIG. 6 illustrates another form of the invention. In this form of the invention, the capsule or cartridge for containing the fluent material is illustrated in the form of a syringe 60 comprising an elongated barrel 61 for containing a predetermined amount of a fluid or liquid-like dental material "M". A plunger 62 having a piston 63 connected to the inner end of the plunger 62 is reciprocally disposed within the barrel 61 of the syringe 60. The other end of the syringe barrel is provided with an end wall 64 having an outlet opening 65 through which the liquid dental material is dispensed when the plunger 62 is pushed to drive the piston 63 toward the outlet opening 64.

In accordance with this invention, a sealing cap 66 is detachably connected to the front or outlet opening 64 of the syringe barrel to seal the same. The sealing cap 66 may be releasably, secured to the syringe barrel by complementary threads or by a Leur lock type of fitting.

To control the dispensing of the liquid dental material from the syringe barrel 61, a detachable nozzle tip 67 is provided, which is adapted to be fitted to the end of the syringe barrel, to define a nozzle upon the removal of the sealing cap 66. As shown, the discharge or nozzle tip 67 is provided with a chamber or tube portion 67A for receiving a filler or filter 68 in the form of porous sponge, foam, cotton or other suitable porous or open cellular material, as hereinbefore described. Thus, when the liquid dental material M is to be dispensed, the sealing cap 65 is removed from the end of the syringe barrel 61 and the discharge tip or nozzle 67 is attached to the front end of the barrel, preferably by a Leur lock type of interconnecting fitting. Thus, as the plunger 62 is advanced into the syringe barrel, the material M is forced out the barrel and through the filler or filter 68 contained within the nozzle tip 67 to control the flow of dental material out through the end of the nozzle tip 67. In this manner, the dentist or operator can dispense the liquid dental material in a controlled manner whereby the porous filler 68 can control the amount of material flowing therethrough, depending upon the amount of compressive force that is imparted onto the plunger 62. It will be understood that the discharge end of the nozzle tip 67 may comprise a needle-like cannula or may be integrally molded to the tube portion 67A. While the invention has been described with respect to a dental capsule, it will be understood that the invention is useful for packaging, storing, and dispensing various types of low viscosity liquid-like fluids for other applications.

While the present invention has been described with respect to particular embodiments thereof, modifications and variations may be made without departing from the spirit or scope of this invention.

What is claimed is:

1. A dental capsule for packaging, storing and dispensing a fluent low viscosity dental material comprising:
   a capsule having a body portion defining a chamber,
   said body portion being open at one end, and
   a discharge nozzle terminating in a discharge orifice connected to the other end of said body portion,
   a filler of cellular sponge-like material disposed in said chamber,
   filler being saturated with a low viscosity dental material,
   and a displaceable piston sealing said open end to confine said saturated filler within said chamber.

2. A dental capsule as defined in claim 1 and including means for sealing said discharge orifice.

3. A dental capsule as defined in claim 2 wherein said last mentioned means comprises a detachable sealing cap.

4. A dental capsule as defined in claim 2 wherein said last mentioned means comprises a sealing cap integrally molded to said discharge nozzle forming a seal for said discharge orifice.

5. A dental capsule as defined in claim 4 wherein said integral sealing cap is connected to said discharge nozzle by a frangible portion.

6. A dental capsule as defined in claim 5 wherein said sealing cap includes means for resealing said discharge orifice.

7. A dental capsule as defined in claim 1 wherein said body portion is cylindrical in shape,
   said body portion being closed at the end opposite said open end,
   and said discharge nozzle being angularly disposed relative to the longitudinal axis of said body portion, and
   a laterally outwardly extending flange circumscribing said open end.

8. A dental capsule as defined in claim 1 wherein said dental material is rendered light sensitive, and
   said capsule being formed of a light opaque material.

9. A capsule for packaging, storing and dispensing a fluent low viscosity material comprising:
   a capsule having a body portion defining a chamber,
   said body portion having an opening at one end thereof, and
   a discharge nozzle connected adjacent the other end of said body portion,
   a porous filler disposed within said chamber between said open end and said discharge nozzle,
   said filler being saturated with a supply of fluent low viscosity material,
   and a displaceable piston sealing said saturated porous filler within said chamber whereby said fluent, low viscosity material is dispensed by displacement of said piston to impart a compressive force on said filler to cause said fluent material to be squeezed out of said porous filler and dispensed through said discharge nozzle in a controlled manner depending upon the amount of compressive force imparted onto said filler.

10. A capsule as defined in claim 9 and including means for sealing said discharge nozzle.

11. A method of dispensing and applying a fluent dental material having a liquid-like consistency comprising the steps of:
    utilizing a capsule having a body portion defining a reservoir,
    placing a filler formed of compressible porous material within said reservoir, saturating said filler with a low viscosity dental material having a liquid-like consistency, sealing said reservoir with a displaceable piston, and imparting a force on said piston to effect a displacement thereof, whereby a compressive force is imparted onto said filler to cause the dental material to be squeezed out of said filler and discharged from said capsule.

12. A method of dispensing and applying a fluent low viscosity dental material having a liquid-like consistency to a tooth comprising the steps of:

utilizing a sponge-like filler saturated with a fluent low viscosity dental material disposed in a dental capsule in a confined manner, imparting a compressive force on said filler to squeeze the fluent, low viscosity dental material out from said filler, and applying said low viscosity dental material being squeezed from said filler directly onto a tooth being worked upon.

13. A syringe for packaging, storing and dispensing a low viscosity, liquid-like dental material directly to the site of use comprising:

an elongated barrel defining a chamber for containing a predetermined amount of fluent liquid-like dental material, said barrel having a front end and a rear end, a plunger reciprocally mounted in said barrel and extending beyond said rear end, a piston connected to the end of said plunger reciprocally mounted within said barrel, said barrel having an end wall adjacent said front end thereof, said end wall having an outlet opening therein, means for sealing said outlet opening when said syringe is inoperative, and a detachable nozzle adapted to be connected in communication with said outlet opening in the operative position, said detahcable nozzle including a tube portion, a discharage nozzle connected to said tube portion, and a porous filler disposed in said tube portion for controlling the flow of dental material therethrough when said plunger and connected piston is displaced to eject the dental material through said outlet opening and connected detachable nozzle.

\* \* \* \* \*